United States Patent [19]

Tu

[11] Patent Number: 5,980,515
[45] Date of Patent: Nov. 9, 1999

[54] DEVICES AND METHODS FOR LEAD EXTRACTION

[75] Inventor: Hosheng Tu, Tustin, Calif.

[73] Assignee: Irvine Biomedical, Inc., Irvine, Calif.

[21] Appl. No.: 08/994,550

[22] Filed: Dec. 19, 1997

[51] Int. Cl.[6] .................................................. A61B 17/39
[52] U.S. Cl. .............................. 606/41; 606/108; 607/116
[58] Field of Search ........................ 606/1, 41, 42, 606/45–52, 108; 607/101, 102, 104, 105, 116

[56] References Cited

U.S. PATENT DOCUMENTS

| | | | |
|---|---|---|---|
| 5,242,441 | 9/1993 | Avitall . | |
| 5,522,875 | 6/1996 | Gates et al. | 607/127 |
| 5,556,424 | 9/1996 | Hocherl | 607/116 |
| 5,620,451 | 4/1997 | Rosborough | 606/108 |
| 5,632,749 | 5/1997 | Goode et al. | 606/108 |
| 5,643,255 | 7/1997 | Organ . | |
| 5,674,217 | 10/1997 | Wahlstrom et al. | 606/15 |
| 5,769,858 | 6/1998 | Pearson et al. | 606/108 |
| 5,779,715 | 7/1998 | Tu | 606/108 |

*Primary Examiner*—Michael Peffley

[57] ABSTRACT

An improved lead extraction system using a rotatable hole saw electrode with a sharp cutting edge that is useful for the extraction and the removal of unwanted lead by a minimal invasive procedure. A lead extraction system suitable for radiofrequency ablation of scar tissues surrounding the implanted lead, is comprised of an outer catheter sheath and an inner delivery catheter having a distal end, a proximal end and at least one lumen extending therebetween, wherein a locking stylet is provided. In one embodiment, the lead extraction system has fluid infusion and irrigation means at its distal tip section and a rotatable hole saw electrode for loosening the target scar tissue by applying radiofrequency energy and cooled fluid to the said electrode and its contacted tissue.

20 Claims, 8 Drawing Sheets

DEVICES AND METHODS FOR LEAD EXTRACTION

FIELD OF THE INVENTION

The present invention generally relates to the improved system for cardiac lead extraction. More particularly, this invention relates to a catheter system and to methods for removing an implanted endocardial pacemaker lead and/or an implanted transvenous defibrillation lead from the cardiovascular system of a patient using a rotatable hole saw electrode and RF energy.

BACKGROUND OF THE INVENTION

Symptoms of abnormal heart rhythms are generally referred to as cardiac arrhythmias. An abnormally rapid rhythm is referred to as tachycardia, while the arrhythmia rates below the normal rhythm are termed bradycardia. Various factors affect the human heart rate and contribute to the changes of rate from what is termed the normal sinus rate range. These rates generally range in adults from 60 to 100 beats per minute. The heart includes a number of normal pathways which are responsible for the propagation of electrical signals from the upper to lower chambers, which are necessary for performing normal systole and diastole function.

Treatment of arrhythmias may be accomplished by a variety of approaches, including drugs, surgery, implantable pacemakers/defibriliators, and catheter ablation. While drugs may be the treatment of choice for many patients, they only mask the symptoms and do not cure the underlying causes. Surgical and catheter-based treatments can only cure some simple cases. Implantable devices correct the arrhythmia and prevent it from occurring unexpectedly.

Cardiac pacemakers, chronically implanted within a patient's body, and connected to the heart by at least one lead, are frequently used to control bradycardiac conditions. Recently, implantable cardioverter-defibrillators, also implanted chronically in a patient's body and connected to the heart by at least one lead, can be used to control tachyarrhythmias and life-threatening fibrillations. There are generally two different types of body implantable leads used with cardiac pacemakers: one type, which requires surgery to expose the myocardial tissue, whereby an electrode is affixed to the epicardial tissue; the second type, which can be inserted through a body vessel, such as a vein, into the heart where an electrode contacts the endocardiac tissue. In the second type, the endocardial lead is often secured to the heart through the endocardial lining by a helix, hook, or tines affixed to the distal end of the lead. When the end of the lead contacts the lining of the heart at a desired location, the lead may be secured in place by utilizing lead securing means, such as screwing the helix into the heart tissue, anchoring the hook or engaging the tines.

Similarly, cardioverter defibrillators have used both epicardial leads, that is, leads with electrodes attached to the outside of the heart, and endocardial leads, that is, leads inserted into the heart through a body vessel.

With either pacing or defibrillation endocardial leads, fibrotic tissue may eventually encapsulate the leads, especially in areas where there is low velocity blood flow. When small diameter veins, through which the lead passes, become occluded with fibrotic tissue, the separation of the lead from the vein is difficult and can cause severe damage or destruction to the vein. Furthermore, separation may not be possible without constricting the movement of the lead.

In most cases, an endocardial lead will outlast its associated implanted device. However, the lead may become inoperative, or another type of lead may be required. Frequently, the existing lead is left in place, and an additional lead is implanted, rather than risking the removal of the old lead, which was now bonded to the surrounding tissue. Leaving the implanted lead in place, however, particularly in the heart, may further restrict the operation of various heart valves through which the lead passes. If several leads are left in place, operative procedures of the heart and its efficiency may be impaired.

In addition, infection may occasionally develop in or around a lead, requiring surgical removal In some cases, surgical removal may involve open heart surgery with its accompanying complications, risks, and costs. These risks are significant for the endocardial pacemaker lead. Because the endocardial defibrillation lead is larger and more complex, the complications associated with the removal of a defibrillation lead can be even greater.

Extraction of chronically implanted leads has been difficult in the past. The problems may include lead fragility and scar tissue encountered along the vein, as well as within the heart. Intravascular countertraction techniques using locking stylets and sheaths via the implant vein, or sheaths, snares, and retrieval baskets via the femoral vein have been described in the literature. Among them, scar tissue was the primary reason for partial or failed removal of a lead. Scar tissue was usually present in multiple locations; the venous entry/subclavian area and the ventricle were the most frequent sites.

Several methods for the removal of pacemaker leads have heretofore been proposed. One method involves a lead removal tool that utilizes a hollow, rigid tube and beveled rod tip for engaging and deforming the coil structure of the heart lead. However, if such a lead can not be removed because of some complication, the tip of the tool is nevertheless locked in place and could not be removed from the lead. Consequently, both the tool and the lead would have to be surgically removed. Moreover, the rigid tube of the tool could easily puncture a blood vessel or a heart cavity wall.

Another method for transvenously extracting a lead involves manual manipulation without the use of an external tool. However, such a method is not possible if the lead has become encapsulated in a blood vessel. Moreover, this method puts excessive strain and tension on the polyurethane or silicone insulation surrounding most pacemaker leads. Should the lead break, the broken inner coil and insulation could damage the heart or surrounding blood vessels. Surgical removal of the broken lead would be imperative. Moreover, if the pacemaker lead included tines, a cork screw, or another fixation device at the tip, pulling on the lead could seriously damage the wall of the heart.

Another technique has been proposed in U.S. Pat. No. 4,943,289. This method generally includes the use of a stiffening stylet, which can be inserted into the lead, and then engages the inner coil of the lead near the tip, allowing tension to be applied through the stiffening stylet close to the tip of the lead. This technique also uses a pair telescopic flexible tubes that are positioned over the lead to free fibrotic connections until the tubes are close to the distal tip of the lead. In a related U.S. Pat No. 5,632,749, Goode et al. teaches the use of an anchoring project or expandable means associated with the apparatus for lead extraction.

Another method has been proposed in U.S. Pat. No. 5,620,451. In this patent, Rosborough teaches the use of a flexible coil of flattened ribbon, whereby a cutting surface is provided at the distal end of the coil. It is also disclosed that the coil is radiopaque so that its use may be observed in the body by fluoroscopy or other suitable means.

What is particular interest to the present invention are radiofrequency (RF) ablation protocols, which have been proven to be highly effective in tissue ablation, while exposing a patient to minimal side effects and risks. Radiofrequency energy is also used in cutting the tissue, or separating implant parts and other substrates. Through a combination of the mechanical rotating force and the radiofrequency energy on a catheter-based device, extraction and removal of an implanted lead becomes feasible and less difficult.

There is therefore a need for a device which comprises a rotatable catheter shaft having a sharp cutting edge with RF energy delivery capability, that is useful for extraction and removal of undesired lead by minimally invasive procedures. It would be desirable for such a system to cut through the scars along an implanted lead by utilizing sharp edges of the electrode above-mentioned with assistance of RF energy for improved lead removal.

SUMMARY OF THE INVENTION

In general, it is an objective of the present invention to provide an improved system for lead removal of both heart pacemaker leads and cardioverter-defibrillator endocardial leads. It is another objective of the present invention to provide an improved lead extraction system with the means of a hole saw electrode, which can be used in ablating an undesired tissue mass, such as scar tissue or a fibrotic attachment at the venous entry/subclavian area and the ventricle surrounding an implanted lead in a minimally invasive manner. Also, another objective of the present invention is to provide a lead extraction system to irrigate the scar tissue site during the lead extraction.

In one embodiment, a lead extraction system is comprised of an outer catheter sheath and an inner delivery catheter. The catheter sheath is semi-flexible, strong and non-conductive, so that the lead extraction system can follow the implanted lead to its distal end where scar tissue is attached, and extract that lead out of a patient. The catheter sheath comprises a distal end, a proximal end, and at least one lumen extended therebetween. The delivery catheter has a distal tip section, distal end, proximal end, and at least one lumen extended therebetween. A handle is secured to the proximal end of the delivery catheter and the catheter sheath. The delivery catheter contains a rotatable hole saw electrode at its distal end. The rotating action of the delivery catheter is controlled at the proximal end of the handle by a rotating mechanism. The delivery catheter can be advanced along the lead to the scar tissue site to dislodge the lead from the said scar tissue by an advancing mechanism at the handle.

The electrode deployment means of the delivery catheter includes a retractable tip section that comprises a hole saw electrode, having a sharp end. In one embodiment, the sharp end has a relatively straight edge. In an alternate embodiment, the sharp end comprises a plurality of sharp points at its edge. In general, the hole saw electrode has a conductive surface for RF energy delivery while the remaining portion of the delivery catheter is not conductive. The tip section has a non-deployed state, when the delivery catheter is positioned inside the catheter sheath. This non-deployed state is maintained during the insertion operation of the lead extraction system into the patient, and during withdrawal of the system from the patient.

The tip section of the delivery catheter has a deployed state when it is advanced out of the distal end of the said catheter sheath. Deployment of the tip section is accomplished by a pushing action on a push-pull mechanism on the handle. Under the deployed state, the delivery catheter has excellent torqueability and also has rotation capability. The degree of deployment is controlled by the pushing action at the push-pull mechanism on the handle and is proportional to the pushing distance on the push-pull plunger which is quantifiable. The rotation of the delivery catheter can be accomplished either manually, mechanically or electromechanically from a rotating means located at the proximal end of the handle.

The deployed hole saw electrode defines an ablation target of the scar tissue covering the implanted lead. The sharp end of the electrode is positioned to directly face the target scar tissue. The said electrode is rotatable and is capable of heating the tissue via RF energy. The advancing operation of the tip section of the delivery catheter is accomplished by pulling back the outer catheter sheath relative to the tip section of the said delivery catheter, so that the tip of the said hole saw electrode firmly contacts and grasps the target scar tissue during an ablation procedure. The degree of advancement is mainly controlled by the pulling action at the push-pull mechanism on the handle.

A conducting wire which is secured to the base of the hole saw electrode means, passes through the lumen of the delivery catheter and through the interior void of the handle, and is thereafter secured to a contact pin of the connector at the proximal end of the handle. Therefrom, the conducting wire is connected to an external RF generator for RF energy delivery.

During lead extraction operations, the lead extraction system, comprised of an outer catheter sheath and an inner delivery catheter, is inserted into the body through a natural body opening by sliding over an existing lead. After the system approaches the target scar tissue mass to be treated, the tip section of the delivery catheter is deployed by being pushed out of the catheter sheath from a push-pull mechanism at the handle. Once positioned, the sharp ends of the hole saw electrode encircles the tissue mass. By a simultaneous or alternate mode, gradually pushing forward the delivery catheter against the tissue mass, rotating the hole saw electrode, and applying RF energy, the target tissue mass is loosened as a result of a combination of the RF energy, mechanical cutting, and the rotating forces of the sharp ends of the hole saw electrode.

A fluid source is positioned at the proximal end of the handle for supplying a fluid flow through the lumen of the said delivery catheter to the tip section, which contains a fluid vent opening. Therefore, at ablation time, the tip section with the hole saw electrode is positioned against the tissues to be ablated. The fluid is continuously or intermittently supplied through the opening to cover and rinse the tissue contact site of the electrodes so that the impedance rise at the contact site is substantially reduced. The appropriate fluid flow rate for fluid irrigation is preferably in the range of 5 cc/min to 20 cc/min. By cooling off the electrode during RF energy delivery, results in optimal ablation efficiency results, and efficient cutting loosens the scar tissues surrounding the implanted lead. Therapeutic fluid can also be supplied through the existing fluid by conveying/ irrigation means.

A fluid conveying lumen is associated with the elongated delivery catheter, and is preferably disposed of within a separate lumen of the delivery catheter along the longitudinal axis thereof The lumen is adapted to communicate with the fluid supplying source, to convey fluid from the source and through the lumen to be discharged through the vent opening of the tip section and diffused out of the tip section containing the hole saw electrode.

This invention also comprises a method and a system for controlling the flow rate of fluid through the lumen to optimize the cooling effect of the energy delivering electrode means of the lead extraction system The control system preferably regulates the flow rate based on signals representative of the temperature of the electrode tip and/or tissue impedance.

In a further embodiment, the material of the electrode is selected from the group of platinum, iridim, gold, silver, stainless steel, and Nitinol. After the lead and its surrounding tissue is loosened, a locking stylet is used to engage the lead with the lead extraction system and the lead is removed by the said lead extraction system thereafter.

The system and methods of the present invention have several significant advantages over the currently known lead extraction systems or methods. In particular, the rotatable hole saw electrode having RF ablation capabilities of this invention results in a more effective means for cutting loose the scar tissue and has a more effective means for removing the undesired lead from the implanted site.

BRIEF DESCRIPTION OF THE DRAWINGS

Additional objectives and features of the present invention will become more apparent and the invention itself will be best understood from the following Detailed Description of the Exemplary Embodiments, when read with reference to the accompanying drawings.

DETAILED DESCRIPTION OF THE EXEMPLARY EMBODIMENTS

Figure 1:
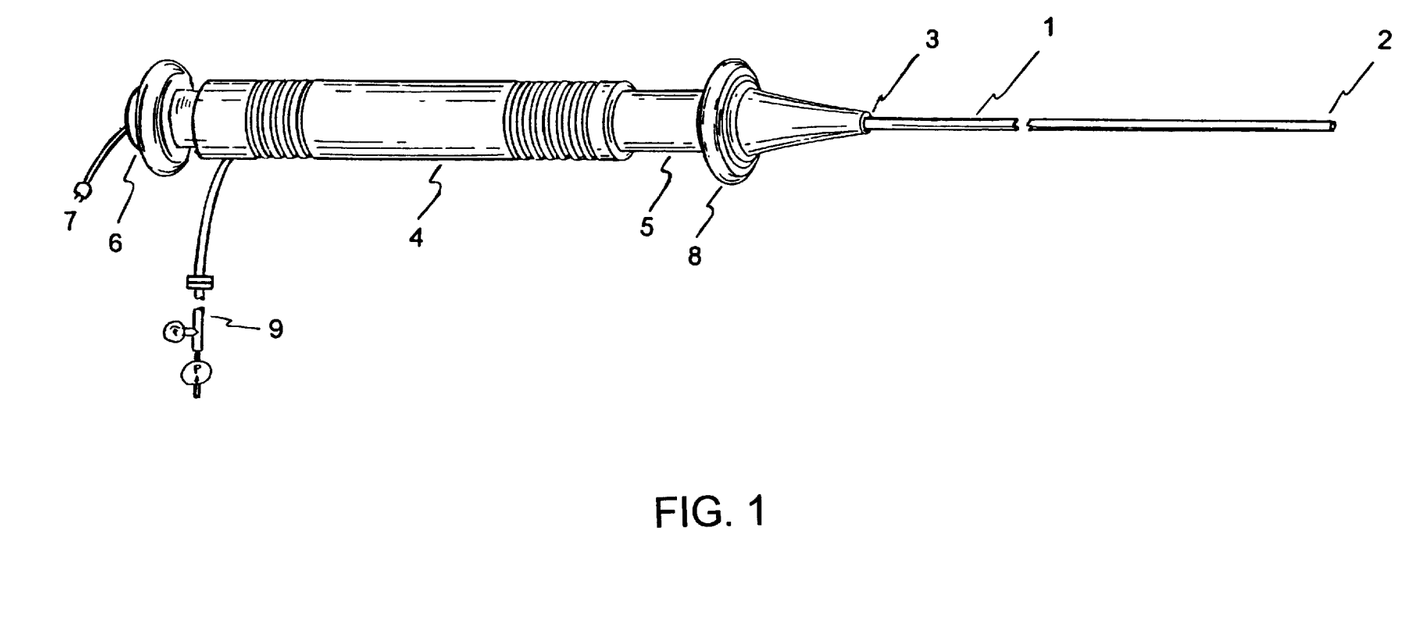
FIG. 1 is an overall view of the lead extraction system containing a rotatable hole saw electrode means at its distal tip section constructed in accordance with the principles of the present invention.

A lead extraction system constructed in accordance with the principles of the present invention is comprised of an outer catheter sheath and an inner delivery catheter wherein their proximal ends are secured to a handle. FIG. 1 shows an overall view of the lead extraction system having a catheter sheath 1, having a distal end 2, a proximal end 3, and at least one lumen extended therebetween. A handle 4 is attached to the proximal end 3 of the said catheter sheath 1. The delivery catheter, which is located within the lumen of said catheter sheath 1, has a distal tip section, distal end, proximal end, and at least a lumen extended therebetween. The proximal end of the delivery catheter is also secured to the handle 4, where there is a push-pull mechanism 5 on the handle 4. A pushing plunger 8 of the push-pull mechanism 5 is used to control the degree of the pushing action. A rotating means 6 is located at the proximal end of the handle 4. The connector means 7 for the conducting wire 13 to be used to transmit the RF energy is located at the very proximal end of the lead extraction system. A fluid irrigation means 9 that contains an external fluid supply source is located close to the proximal end of the handle 4.

Figure 2:
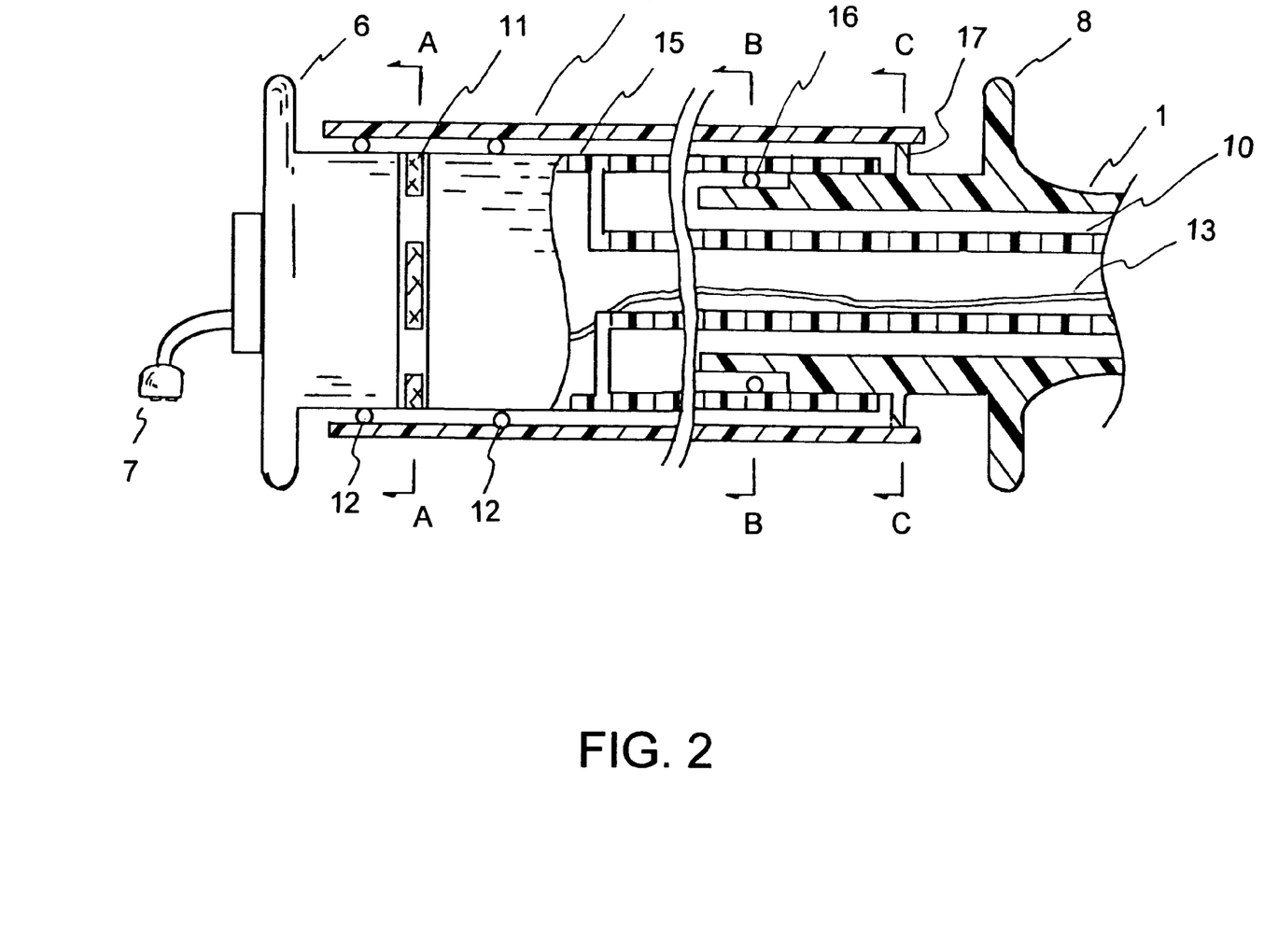
FIG. 2 is a cross-sectional view of the handle portion of the lead extraction system of the present invention.
Figure 5:
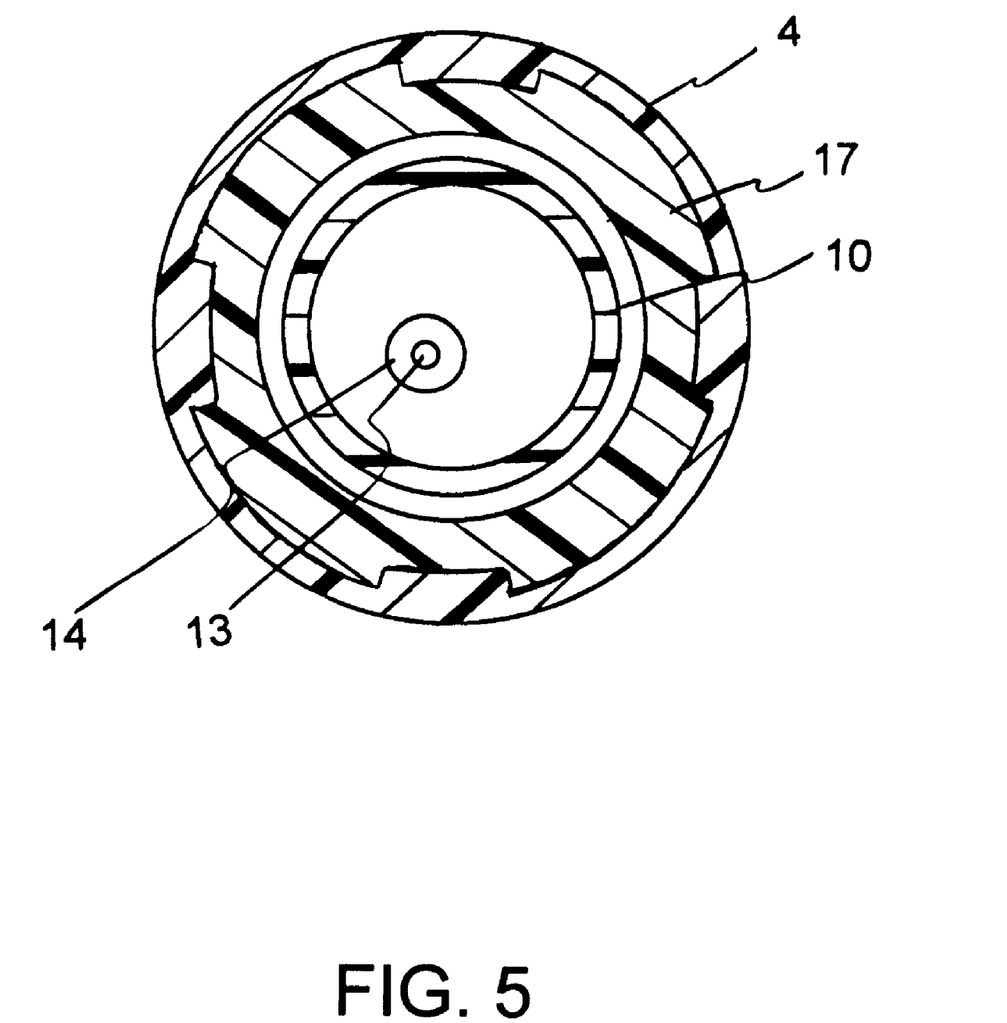
FIG. 5 is a side view of the C—C section of FIG. 2, showing the attachment of the outer catheter sheath and the handle.

FIG. 2 shows a cross-sectional view of the handle portion 4 of the lead extraction system, which is comprised of an outer catheter sheath I and an inner delivery catheter 10. The catheter sheath 1 can be pushed or pulled longitudinally, relative to the handle 4. However, it is maintained stationary circumferentially, relative to the handle. In other words, when the inner delivery catheter is rotated relative to the handle, the outer catheter sheath does not rotate at all. This is shown in FIG. 5 where the C—C section is illustrated. The delivery catheter 10 is secured to the rotating means 6 at the proximal end of the handle portion. The rotating means 6 has a plurality of fluid inlet ports 11. The fluid from an external fluid irrigation means 9 is introduced through an opening at the handle 4 and thereafter through the inlet ports 11 into the lumen of the rotating means 6. The fluid is confined by two O-rings 12 between the handle 4 and the rotating means 6. The fluid is further confined within the lumen of the delivery catheter 10 when the fluid flows down to the distal end of the said delivery catheter.

Figure 3:
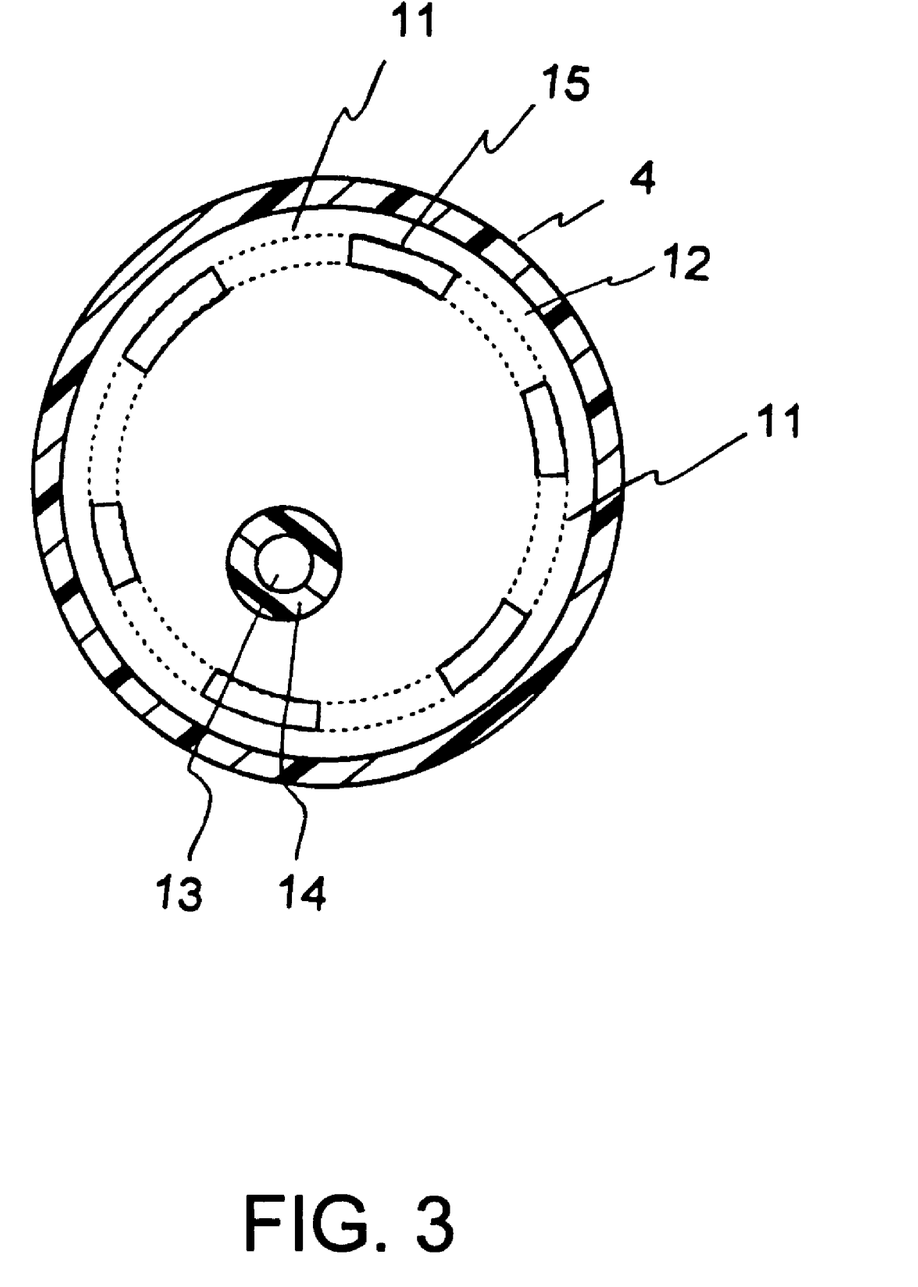
FIG. 3 is a side view of the A—A section of FIG. 2, showing the fluid conveying means of the delivery catheter.

FIG. 3 is a side view of the A—A section of FIG. 2, which shows the fluid conveying means of the delivery catheter 10. Two O-rings 12 are located between the handle 4 and the outer surface 15 of the rotating means 6. The rotating means 6 has a plurality of fluid inlet ports 11. A conducting wire 13 for RF energy transmission with its insulation 14 is located within the lumen of the rotating means 6.

Figure 4:
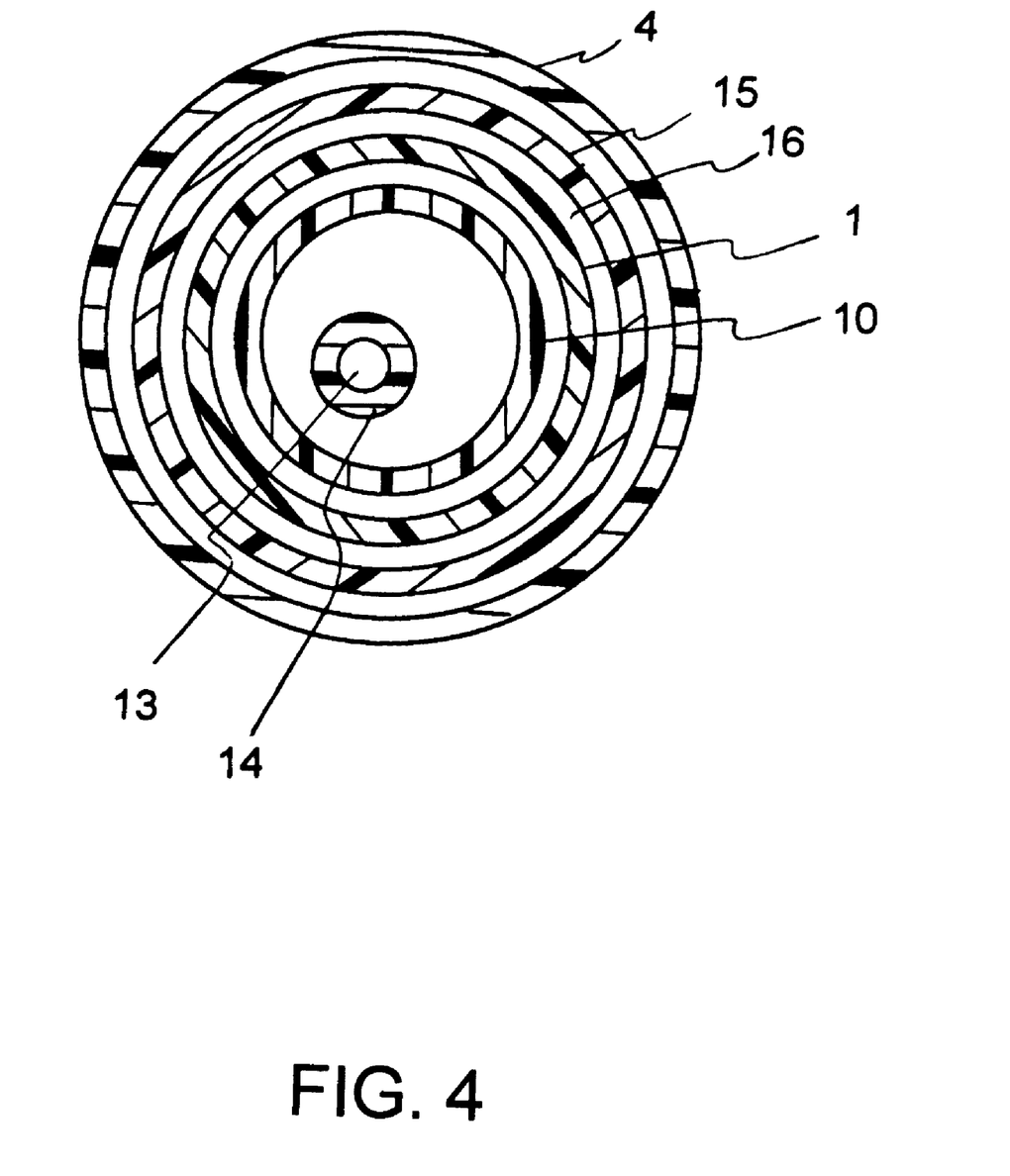
FIG. 4 is a side view of the B—B section of FIG. 2, showing the O-ring portion between the outer catheter sheath and the inner delivery catheter.

FIG. 4 is a side view of the B—B section of FIG. 2, which shows the O-ring portion between the outer catheter sheath 1 and the inner delivery catheter 10. An O-ring 16 is located between the outer surface 15 of the rotating means 6 and the proximal section of the catheter sheath 1. The rotating means 6 is firmly connected to the delivery catheter 10 so that a true 1:1 rotating ratio between the rotating means and the delivery catheter is maintained.

FIG. 5 is a side view of the C—C section of FIG. 2, which shows the attachment of the outer catheter sheath 1 and the handle 4 at the contacting joint 17. A pushing plunger 8 of the push-pull means 5 on the outer catheter sheath I is located adjacent to the handle 4. The catheter sheath can be pushed or pulled relative to the handle. However, the pushing plunger 8 on the catheter sheath 1 is interconnected with the handle 4 at the contacting joint 17 so that the catheter sheath can not rotate relative to the handle.

Figure 6:
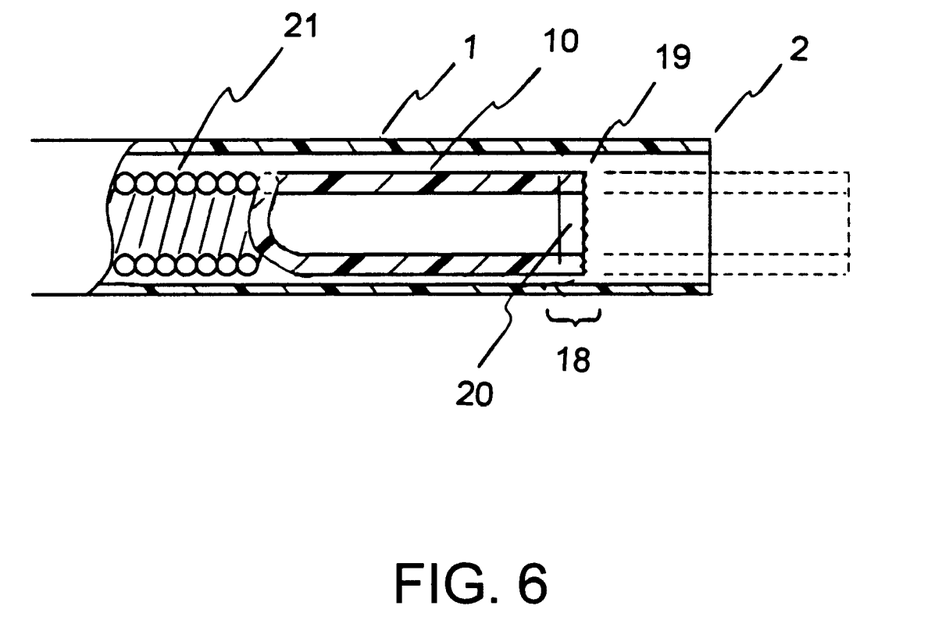
FIG. 6 is a cross-sectional view of the distal tip section of the lead extraction system of the present invention.

FIG. 6 is a cross-sectional view of the distal tip section of the lead extraction system of the present invention. The catheter sheath 1 has a distal end 2 while the delivery catheter 10 comprises a distal tip section 18, a distal end 19 and a hole saw electrode 20. Under a non-deployed state, the delivery catheter 10 is located within the lumen of the catheter sheath 1. Upon electrode deployment, the distal tip section 18 of the delivery catheter 10 is pushed out of the tip 2 of the catheter sheath 1. To improve its flexibility and torqueability, a portion of the delivery catheter 10 can contain a coil wire 21, which can also serve as the transmission means for RF energy delivery to the electrode 20.

Figure 7:
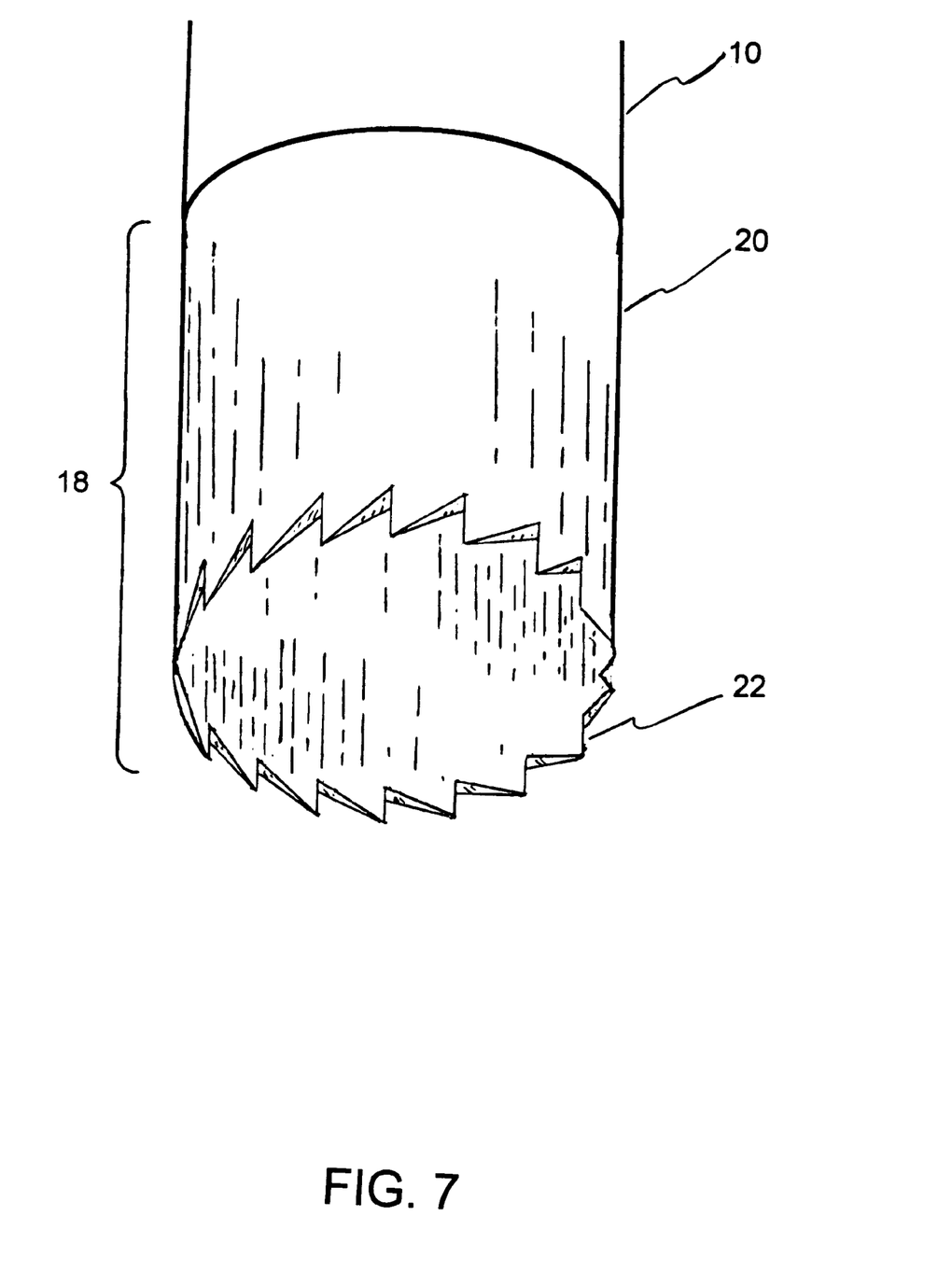
FIG. 7 is a close-up view of the hole saw electrode of the present invention.

FIG. 7 is a perspective view of one type of a hole saw electrode 20. The electrode is located at the distal tip section 18 of the delivery catheter 10. The electrode portion is conductive and can deliver RF energy when it contacts the tissue. The sharp edge 22 of the hole saw electrode 20 is used to cut through the scar tissue associated with the implanted lead. The cutting operation is achieved by a combination of rotating the hole saw electrode, advancing the hole saw electrode, and/or heating the hole saw electrode.

In a further embodiment, the lead extraction system may further comprise a stylet locking mechanism at the handle 4 for controlling the advancement and locking activities of the locking stylet of the delivery catheter 10. A stylet locking plunger of the locking mechanism at the handle is used to control the degree of the advancement of the locking stylet of the delivery catheter. The stylet locking mechanism on the lead extraction system is well-known to those who are skilled in the art.

In an additional embodiment, the lead extraction system further comprises a temperature sensing and close-loop temperature control mechanism for the hole saw electrode having a temperature sensor mounted on the electrode close to the tissue contact site. Temperature sensing wires (not shown) along with a thermocouple or thermistor means is provided to transmit the temperature data from the tissue contact site to an external temperature measuring and control apparatus. An algorithm is equipped for the ablation system so that a close-loop temperature control is effective and the temperature data is relayed to an external RF generator (not shown) for controlled energy delivery.

Figure 8:
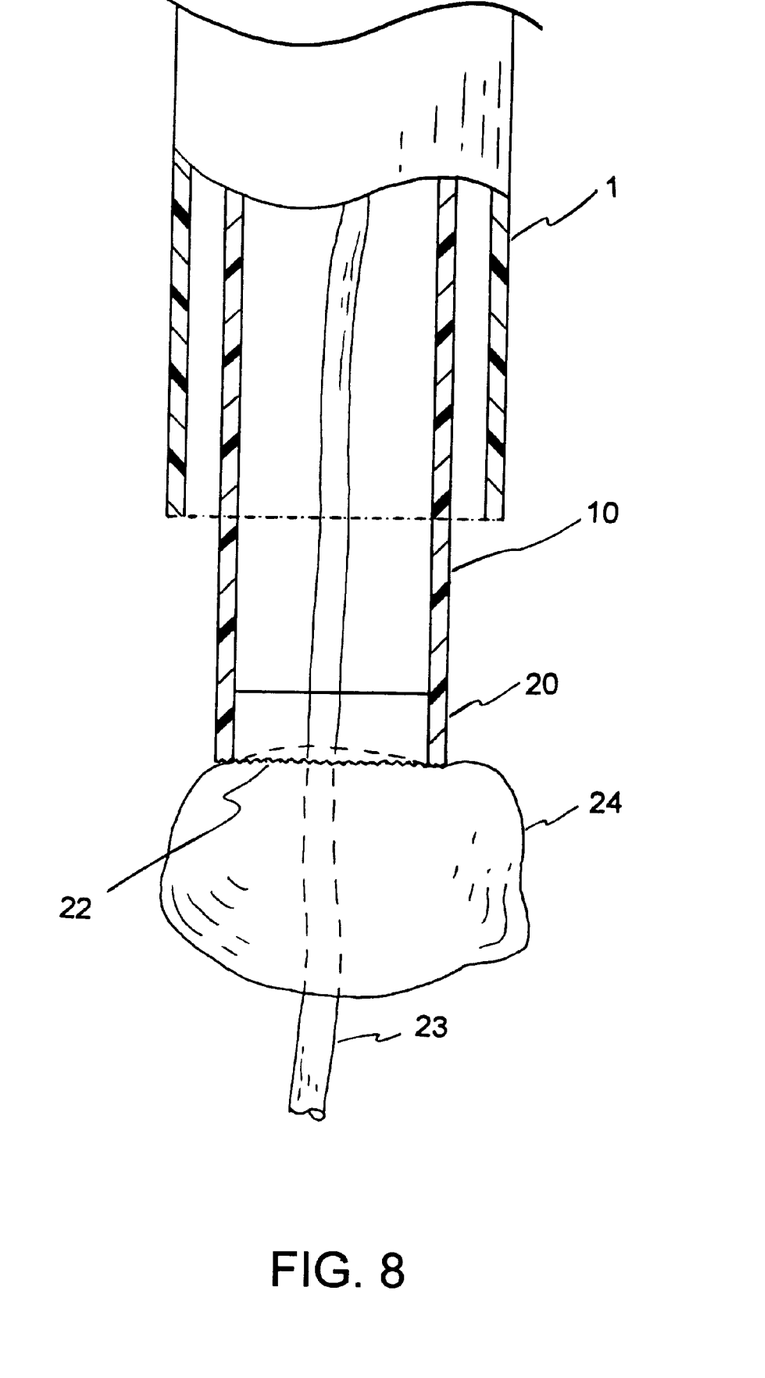
FIG. 8 is a simulated lead extraction operation of the lead extraction system on an implanted lead.

FIG. 8 is a close-up view of the lead extraction operation of the lead extraction system. An implanted lead 23 with its surrounding scar tissue 24 is to be removed from the body of a patient. The hole saw electrode 20 is positioned to have its sharp edge 22 contacting the scar tissue. The delivery catheter 10 is located within the lumen of the catheter sheath 1. The delivery catheter is capable of rotation, while the catheter sheath is stationary. By way of illustration, a lead extraction system of this invention is inserted along or is slid over the existing lead wire through a vein. The system is positioned near the target tissue site where the delivery catheter contacts the tissue. The delivery catheter is deployed and the sharp edge of the electrode firmly contacts the tissue to be ablated. By a combination of the following actions: gradually pushing forward the delivery catheter against the tissue mass, rotating the hole saw electrode, and applying RF energy to the hole saw electrode, the target tissue mass is loosened. Thereafter, the lead can then be removed with ease.

From the foregoing, it should now be apparent that an improved lead extraction system comprised of a rotatable hole saw electrode with RF energy delivery capability has been disclosed for removing the implanted lead from a patient. While this invention has been described with reference to a specific embodiment, the description is illustrative of the invention and is not to be construed as limiting the invention. Various modifications and applications may occur to those skilled in the art without departing from the true spirit and scope of the invention as described by the appended claims.

What is claimed is:

1. A lead extraction system comprising:
   a catheter sheath having a distal end, a proximal end, and at least one lumen extending therebetween;
   a handle attached to the proximal end of the catheter sheath;
   a delivery catheter inside the catheter sheath, the delivery catheter having a distal tip section, a distal end, a proximal end, and at least one lumen extending therebetween, wherein a hole saw electrode is disposed at the distal end of said delivery catheter, and wherein the proximal end of said delivery catheter is secured to the handle; and
   a deployment means for the distal tip section of said delivery catheter to be deployed out of the distal end of the catheter sheath.

2. The lead extraction system as in claim 1, further comprising RF energy means to deliver RF energy to the hole saw electrode.

3. The lead extraction system as in claim 1, further comprising a locking stylet located within the lumen of said delivery catheter.

4. The lead extraction system as in claim 1, further comprising fluid irrigation means for supplying fluid from an external fluid supply source to the distal tip section of the delivery catheter and venting the fluid out of the distal end of said delivery catheter.

5. The lead extraction system as in claim 4, wherein the fluid is selected from the group consisting of saline, heparin, antibiotics, chemotherapy and therapeutics fluids.

6. The lead extraction system as in claim 2, wherein said hole saw electrode has a sharp edge.

7. The lead extraction system as in claim 2, wherein said hole saw electrode contains a plurality of sharp points at its edge.

8. The lead extraction system as in claim 2, wherein said delivery catheter is rotatable.

9. The lead extraction system as in claim 2, further comprising at least one temperature sensor mounted on the hole saw electrode and a closed-loop temperature control mechanism for the hole saw electrode, wherein temperature sensed from the at least one temperature sensor is transmitted to the closed-loop temperature control mechanism for controlling energy delivery.

10. The lead extraction system as in claim 4, further comprising means for controlling flow rate of the fluid through the at least one lumen of the delivery catheter, wherein the means for controlling the flow rate is based on signals representative of temperature sensed by the at least one temperature sensor.

11. The lead extraction system as in claim 2, wherein the hole saw electrode is made from a material selected from the group consisting of platinum, iridium, gold, silver, stainless steel, and Nitinol.

12. A method for operating a lead extraction system, the lead extraction system comprising an outer catheter sheath, an inner delivery catheter, a locking stylet, and a rotatable hole saw electrode mounted at a distal end of said inner delivery catheter, the method comprising the steps of:
    (a) sliding the lead extraction system over an existing lead in a patient, wherein the existing lead is surrounded by scar tissue;
    (b) intimately contacting a distal end of the outer catheter sheath with the scar tissue;
    (c) deploying the inner delivery catheter that comprises the hole saw electrode;
    (d) applying RF energy to the hole saw electrode while cutting through the scar tissue by simultaneously advancing and rotating the inner delivery catheter, wherein the RF energy is provided by an external RF energy generating means through an electrical conductor to the hole saw electrode;
    (e) engaging the locking stylet onto the lead; and
    (f) extracting the lead by pulling the lead extraction system out of a patient.

13. The method for operating a lead extraction system as in claim 12, further comprising a step of supplying fluid to the hole saw electrode of the delivery catheter, wherein the fluid is supplied from an external fluid supply source and vented out of the distal end of said inner delivery catheter.

14. A lead extraction system comprising:
   a catheter sheath having a distal end, a proximal end, and at least one lumen extending therebetween;
   a handle attached to the proximal end of the catheter sheath;
   a delivery catheter inside the catheter sheath, the delivery catheter having a distal tip section, a distal end, a proximal end, and at least one lumen extending therebetween, wherein a hole saw electrode means is disposed at the distal end of said delivery catheter, and wherein the proximal end of said delivery catheter is secured to the handle;
   a deployment means for the distal tip section of said delivery catheter to be deployed out of the distal end of the catheter sheath; and
   RF energy generating means for supplying RF energy to said electrode means.

15. The lead extraction system as in claim 14, further comprising fluid irrigation means for supplying fluid from an external fluid supply source to the distal tip section of the delivery catheter and venting the fluid out of the distal end of said delivery catheter.

16. The lead extraction system as in claim 15, wherein the fluid is selected from the group consisting of saline, heparin, antibiotics, chemotherapy and therapeutics fluids.

17. The lead extraction system as in claim 14, further comprising a locking stylet located within the lumen of said delivery catheter.

18. The lead extraction system as in claim 14, wherein the delivery catheter is rotatable.

19. The lead extraction system as in claim 14, wherein said electrode means has a sharp edge.

20. The lead extraction system as in claim 19, wherein said electrode means contains a plurality of sharp points at its edge.

* * * * *